United States Patent
Lenz

(10) Patent No.: US 9,329,403 B2
(45) Date of Patent: May 3, 2016

(54) SPECTACLES HAVING A RETAINING STRAP

(71) Applicant: Eberhard Lenz, Stuttgart (DE)

(72) Inventor: Eberhard Lenz, Stuttgart (DE)

( * ) Notice: Subject to any disclaimer, the term of this patent is extended or adjusted under 35 U.S.C. 154(b) by 316 days.

(21) Appl. No.: 13/923,976

(22) Filed: Jun. 21, 2013

(65) Prior Publication Data

US 2013/0278883 A1 Oct. 24, 2013

Related U.S. Application Data

(63) Continuation of application No. PCT/EP2011/006442, filed on Dec. 20, 2011.

(30) Foreign Application Priority Data

Dec. 21, 2010 (WO) .................. PCT/EP2010/007816

(51) Int. Cl.
| | |
|---|---|
| G02C 5/14 | (2006.01) |
| G02C 3/00 | (2006.01) |
| G02C 11/02 | (2006.01) |
| A61F 9/02 | (2006.01) |

(52) U.S. Cl.
CPC .............. *G02C 3/006* (2013.01); *A61F 9/027* (2013.01); *G02C 3/003* (2013.01); *G02C 11/02* (2013.01)

(58) Field of Classification Search
CPC .. G02C 3/003; G02C 2200/08; G02C 5/2209; G02C 2200/06; G02C 11/02; G02C 1/08; G02C 9/00; G02C 2200/04; G02C 3/006; G02C 9/04; G02C 1/10; G02C 5/001; G02C 5/20; G02C 5/146; A61F 9/02; A61F 9/027
USPC ........... 351/156, 157, 111, 121, 123, 154, 41, 351/86
See application file for complete search history.

(56) References Cited

U.S. PATENT DOCUMENTS

| | | | | |
|---|---|---|---|---|
| 2,798,409 | A | * | 7/1957 | Speers ........................ 351/157 |
| 4,515,449 | A | * | 5/1985 | Davidson ..................... 351/156 |
| 4,976,531 | A | * | 12/1990 | Kahaney ...................... 351/156 |
| 5,673,094 | A | | 9/1997 | Bahouth |
| 5,786,882 | A | | 7/1998 | Satterthwaite |
| 6,182,334 | B1 | * | 2/2001 | Davancens ....................... 24/3.3 |

(Continued)

FOREIGN PATENT DOCUMENTS

| | | |
|---|---|---|
| DE | 84 14 889 U1 | 10/1984 |
| DE | 93 20 854 U1 | 6/1995 |

(Continued)

*Primary Examiner* — Huy K Mai
*Assistant Examiner* — Daniele Manikeu
(74) *Attorney, Agent, or Firm* — Muncy, Geissler, Olds & Lowe, P.C.

(57) ABSTRACT

Spectacles having a lens frame and arms connected thereto and a retaining strap which can be fastened to the spectacles. A receiving device is provided on the free end of at least one arm, which receiving device interacts with a connecting element to which a retaining strap is undetachably fastened, e.g. moulded on. A plurality of receiving devices can be disposed at predetermined positions between the front end of each arm and the free end thereof. This has the advantage that the retaining strap can be adapted individually to the shape of the head, the hair length and possible individual preferences of the wearer of the spectacles. Thus the retaining strap can be immovably fastened not only to the free end of the arm but also to a front end of the arm, that is to say where the arm adjoins the hinge, and all intermediate positions.

14 Claims, 3 Drawing Sheets

(56) References Cited

U.S. PATENT DOCUMENTS

| | | |
|---|---|---|
| 6,253,388 B1 | 7/2001 | Lando |
| 6,478,419 B1 | 11/2002 | McDaniel |
| 2003/0101542 A1 | 6/2003 | Mackay et al. |
| 2004/0051845 A1* | 3/2004 | Steere .......................... 351/157 |
| 2008/0309869 A1 | 12/2008 | Chen |
| 2009/0135369 A1* | 5/2009 | Burnstein ..................... 351/52 |
| 2010/0265453 A1* | 10/2010 | Lampru ............... G02C 11/02 351/52 |
| 2013/0037431 A1* | 2/2013 | Lin .......................... A45F 4/12 206/278 |

FOREIGN PATENT DOCUMENTS

| | | |
|---|---|---|
| DE | 93 20 854 U1 | 8/1995 |
| DE | 100 57 908 A1 | 7/2001 |
| FR | 2 803 923 A1 | 7/2001 |

* cited by examiner

SPECTACLES HAVING A RETAINING STRAP

This nonprovisional application is a continuation of International Application No. PCT/EP2011/006442, which was filed on Dec. 20, 2011, and which claims priority to International Application No. PCT/EP2010/007816, which was filed on Dec. 21, 2010, and which are both herein incorporated by reference.

BACKGROUND OF THE INVENTION

1. Field of the Invention

The present invention relates to eyeglasses having a retaining strap and a retaining strap.

2. Description of the Background Art

In the case of eyeglasses used only for reading or as safety glasses for special operations or also as sunglasses and sports glasses, it is often useful that the eyeglasses can be carried along without storing them in a case or in some other fashion. For these cases, a retaining strap or a chain placed around the neck is often used, which can be connected to the eyeglasses in different ways.

A solution disclosed in DE 84 14 889 U1 consists of pulling flexible loops made of rubber or plastic through a tube or a coil and of slipping one of their ends over the temple arm and fastening the other to the retaining strap or chain. This very simple type of securing the retaining strap or chain to the eyeglasses is very unreliable, however, because both a frequent moving of the strap on the temple arm cannot be avoided and there is also the risk that after prolonged use the connection loosens and the eyeglasses fall. In addition, prior-art retaining straps or chains are normally so long that the eyeglasses hang in front of the body in an uncontrolled fashion and can be damaged thereby or limit the freedom of movement, which is also disadvantageous.

U.S. Pat. No. 6,182,334 B1 describes a connection between a retaining strap and the temple arm by means of a rubber tube, which is pushed over the ends of the temple arms. The disadvantage here is that the diameter of the tube connections must be matched to the thickness of the arms. Other disadvantages are that the connection looks makeshift and that the tube pushed onto the temple arms has a negative impact on wearing comfort.

Another approach is described in DE 10057908 C2 or the corresponding U.S. Pat. No. 6,253,388 B1. Here, the retaining strap was proposed as so short that the eyeglasses are retained separately on the bridge of the nose and with a magnet connector. Because of the otherwise resulting instability of both halves of the eyeglasses, the retaining strap is formed as a rigid strap. This rigid design due to the structure has considerable disadvantages. Thus, for instance, the eyeglasses cannot be put into the pocket compactly packed but remain bulky. In addition, in the case of a leaning head, as perhaps during reading in bed, the rigid strap negatively affects the fit of the eyeglasses.

US 2004/0051845 A1 has the object of disclosing eyeglasses with a retractable retaining strap. In FIG. 1 of the publication, a retaining strap is shown, which is either threaded into a hollow arm and is attached at the end over a roller or connected with a lock to the arm. For connecting the retaining strap with a connecting element it is disclosed that a sphere is attached at the end of the retaining strap.

U.S. Pat. Nos. 6,478,419 B1 and 5,673,094 A disclose floatable eyeglasses, in which the retaining strap provides buoyancy. In U.S. Pat. No. 6,478,419 B1, only the two ends of a hollow retaining strap are put over the free ends of the arms. Therefore this is a detachable connection.

U.S. Pat. No. 5,786,882 A, like DE 93 20 854 U1, has the object of keeping the retaining strap securely and reliably on the eyeglasses. The proposed solution in the applicant's opinion is aesthetically unsatisfactory.

US 2003/0101542 A1, like the aforementioned U.S. Pat. No. 6,182,334 B1, has the object of connecting a retaining strap made of woven cloth material to eyeglasses. To this end, the retaining strap is connected via connecting elements to the arms. The fastening to the connecting elements occurs with receiving parts, which are suitable for receiving a woven cloth material. US 2003/0101542 A1 shows a retaining strap which can be attached to the temple arms and to the arm ends. In case of attachment to arms, however, it is not fixed in one position but can be moved along a straight part of the arm. This results in limited wearing comfort, because the attachment of the retaining strap can move during wearing and the requirements in the case of long hair are different than in the case of short hair.

In the closest DE 93 20 854 U1, eyeglasses with an eyeglass rim and arms connected thereto are proposed, which have at least one retainer, connected detachably to the eyeglass rim or the arms, for a retaining strap. The detachable connection occurs by means of a plug-/snap-in connection. This is achieved in that a specially constructed retainer connected by means of straps to the retaining strap engages into in a matching seat in the rim or arm. The disadvantage of the proposed design by means of the two-armed U-shape of the retainer is that the receiving device because of the enclosing by the U-shaped retainer on both sides is always prominently visible on the eyeglasses, i.e., also without attachment of a retaining strap. DE 93 20 854 U1 has the object of keeping the retaining strap securely and reliably on the eyeglasses. The proposed solution, however, is aesthetically unsatisfactory in the applicant's opinion.

SUMMARY OF THE INVENTION

It is therefore an object of the present invention to refine eyeglasses with a retaining strap such that the connection between the eyeglasses and the retaining strap is improved both in the functional and aesthetic aspect.

The present invention, in an embodiment, attains the object in that an arm has a receiving device at the front end of the arm, which can interact with a connecting element of a retaining strap, and in addition a further receiving device, which can interact with the connecting element of a retaining strap and form a detachable connection, is provided at the free end of an arm. As a result, the retaining strap can be attached immovably not only to the free end of the arm but also to a front end of the arm, therefore where the arm adjoins the hinge. The attachment of the retaining strap cannot move when worn and the eyeglasses with the retaining strap are equally adaptable with an adjustable ideal hold point to the requirements in the case of long hair (front position) and short hair (back position).

It is provided in an embodiment that a plurality of receiving devices are disposed between the front end of each arm and the free end thereof at predetermined positions. This has the advantage that the retaining strap can be adjusted individually to the shape of the head, hair length, and possible individual preferences of the eyeglass wearer.

It is provided in an embodiment that the two connecting elements of the retaining strap can form a detachable connection with the associated arm by means of a snap fastener, slotted hole, plug, or plug-/snap-in connection, whereby the outer side of an arm has no hole and if need be a hole can be provided at the free end of the arm for connection to the connecting element. It is therefore not obvious that when the eyeglasses are worn without a retaining strap, all options have been provided so that a retaining strap according to the invention can be attached immovably to them.

The invention also relates to a retaining strap for interacting with eyeglasses of the invention. A connecting element, which can interact with a receiving device on the arm, is attached undetachably at the ends of the retaining strap. The attachment can occur between the retaining strap and the connecting element in all known fashions; integral molding is especially advantageous in that the connecting element is surrounded or penetrated undetachably by the material of the integrally molded retaining strap.

"Integral molding" is a term known in plastics technology and is clear to the person skilled in the art of plastics technology, particularly joining technology. Various methods are known, for which reason the applicant in the present patent application does not wish to commit himself to a common method. A known method is, e.g., injection molding in a mold in which a part is placed before the injection process and an inseparable connection results after curing, e.g., by cooling. Reference is also made repeatedly in the description to typical process steps of an injection molding process, so that it is clear to the person skilled in the art what is meant by "integrally molded." In particular, the connecting element has serrations or openings, which are surrounded or penetrated by the material of the integrally molded retaining strap.

An aesthetically pleasing solution results when there is a continuous transition from the retaining strap to the connecting element. Alternatively or in addition, the connecting element can be made of the same material as the arm.

Overall, the transition between the arm and retaining strap is designed as aesthetically pleasing. This occurs, e.g., by continuous material transitions between connecting elements, on the one hand, and the retaining strap, on the other, in that the retaining strap is integrally molded. The pleasing design of the transition between the arm and retaining strap also results from the use of the same materials for the arm and connecting element. None of the listed citations provide this type of solution.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
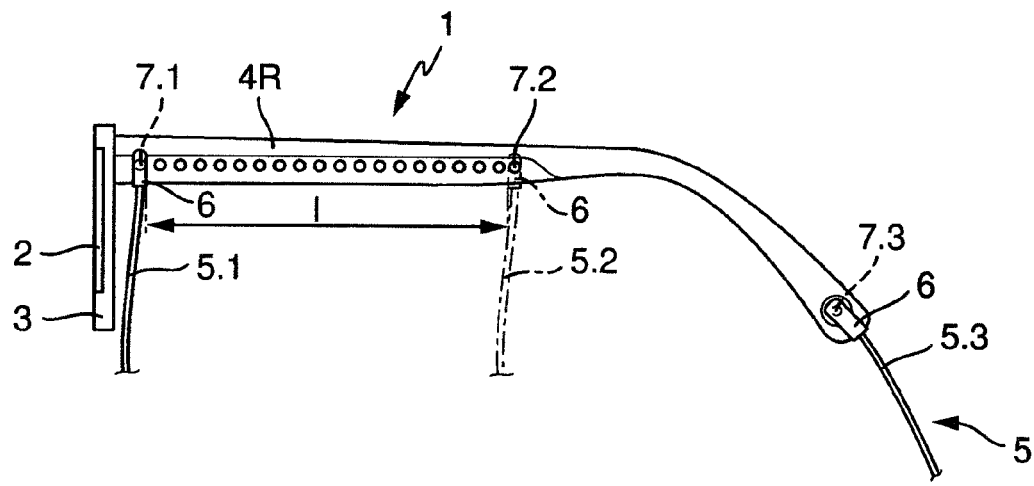
FIG. 1 shows a side and inside view of an arm.

FIG. 1 shows in a side view and in an inside view an exemplary embodiment of eyeglasses 1 with a retaining strap 5. Eyeglasses 1 comprise glass lenses 2 and a rim 3. The right arm 4R is shown in an inside view. The left arm in this view would cover the right arm 4R and is therefore not shown. A retaining strap 5.1 in a front position, a retaining strap 5.2 in a back position disposed at a distance I, and a retaining strap 5.3 in an end position at the free end of arm 4R are shown in FIG. 1.

In general receiving devices 7 for connecting elements 6 are to be disposed and configured with retaining strap 5 so that in the separated state when the eyeglasses are worn they are not perceived by the observer or at least not perceived as interfering; i.e., they are either not visible or appear to be an integral part of the eyeglass design. The illustrated embodiments are to be understood only as examples. Differences can arise in a specific design, without this deviating from the illustrated inventive concept.

To be able to make a retaining strap as short as possible, which is so short that the eyeglasses cannot be easily put on or taken off over the head, the retaining strap can be made elastic and in addition or alternatively be provided with an fastener that can be opened.

For an optimal design of the connection between retaining strap 5 and the eyeglass frame, having a rim 3 and the two arms 4R, 4L, from a functional and aesthetic aspect, various detachable connections of the retaining strap with eyeglass frame 3, 4R, 4L in the transitional region between arm 4R and retaining strap 5 are proposed below. The detachable connection occurs by means of receiving devices 7.1-7.3 disposed similarly on both arms 4R, 4L at predetermined positions and the retaining strap 5.1-5.3 in corresponding attachment positions. The attachment of retaining strap 5 occurs at predetermined positions P1, P2, P3 by means of connecting element 6. Here, an elastic retaining strap 5 is assumed, whereby a non-elastic retaining strap is also conceivable, however.

When retaining strap 5.3 is in the $3^{rd}$ position, the two arms 4R, 4L are continued visually so that they flow into a retaining strap by means of a receiving device 7.3 and a connecting element 6, so that the free ends of retaining strap 5 attach directly to the free ends of arms 4R, 4L.

The detachable connection assures that retaining strap 5 is not constantly connected to eyeglasses 1, but only when the eyeglass wearer desires it. If eyeglasses 1 are to be used without retaining strap 5, the strap can be removed by releasing the connection with little force. In addition, retaining straps different with regard to material, color, and length can be used by the user. Thus, the wish of very many people to have eyeglasses always at hand, whether reading glasses, sunglasses, or safety glasses, is fulfilled simply but effectively from the technical aspect and very flexibly from the design aspect. The proposed solutions are designed in part so that connecting element 6 is pivotable in the respective receiving device 7.1-7.3, so that retaining strap 5 can also be angled flexibly in an established position to arm 4R, 4L. The detachable connection can be provided on both arms 4R, 4L. However, the detachable connection on one arm can be combined with an undetachable connection on the other arm. However, both connections can also be undetachable, e.g., due to integral molding.

Figure 2:
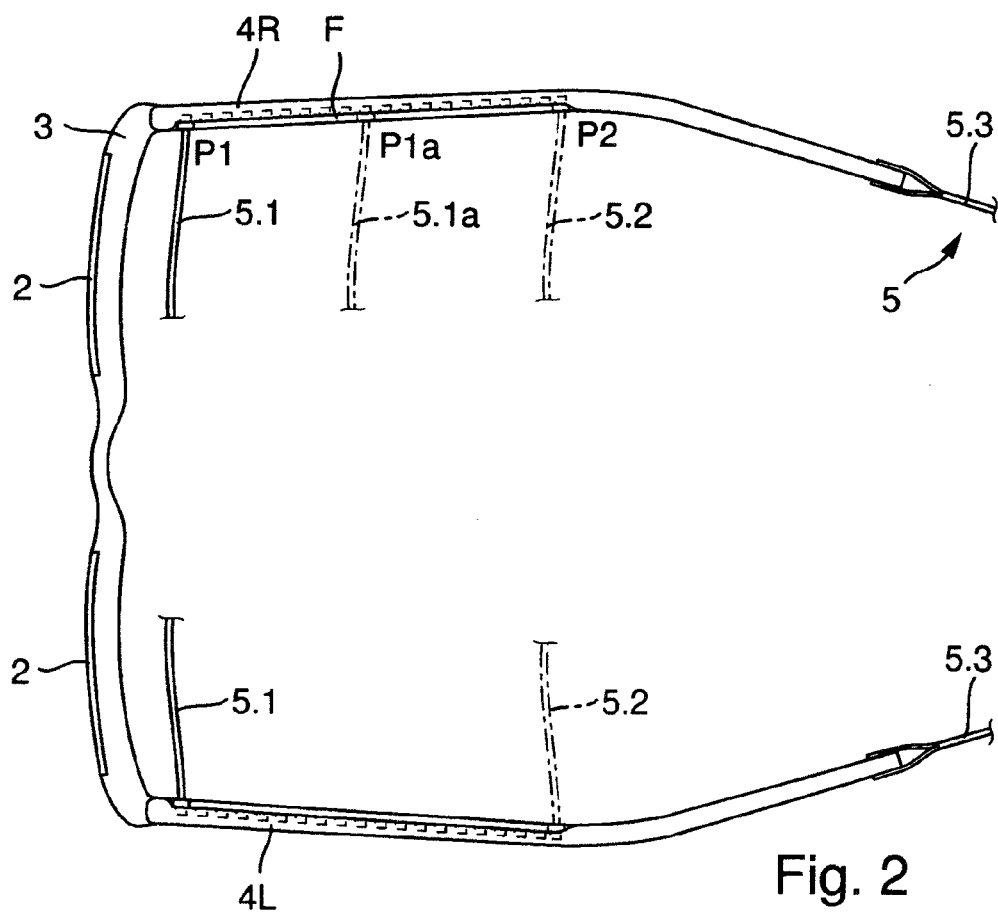
FIG. 2 shows a view of the eyeglasses with the retaining strap in 3 positions.

In order to achieve that receiving devices 7.1-7.3 are not visible as such, also when retaining strap 5 is removed, they must be either inconspicuous or an integral part of the design of the eyeglasses. FIG. 2 shows a view of the eyeglasses with the retaining strap in 3 positions for retaining strap 5. It is provided in this exemplary embodiment that receiving devices 7.1 and 7.2 are arranged in a groove F and receiving devices 7.1-7.2 are not visible along the arm on the outer side, therefore the visible side of the arm, in that the holes are not made as through holes. Depending on the selection of the hole, retaining strap 5 is attached in the first P1, second P2, or third position P3. Intermediate positions P1a are also conceivable, which are disposed along segment I (FIG. 1) between the $1^{st}$ position P1 and the $2^{nd}$ position P2.

Figure 3A:
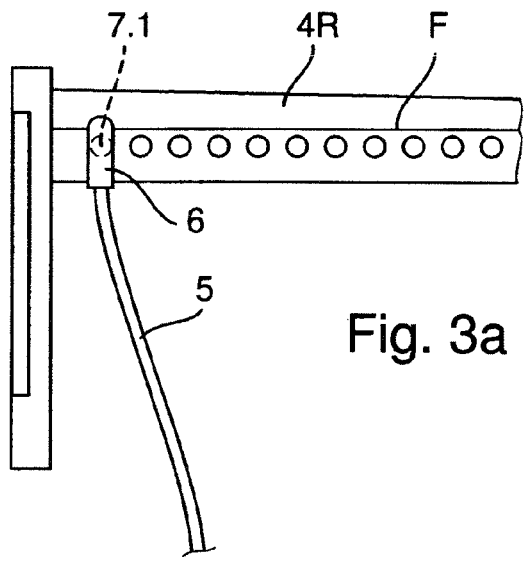
FIGS. 3a and 3b show a detail view of the arm and a cross section thereof.
Figure 3B:
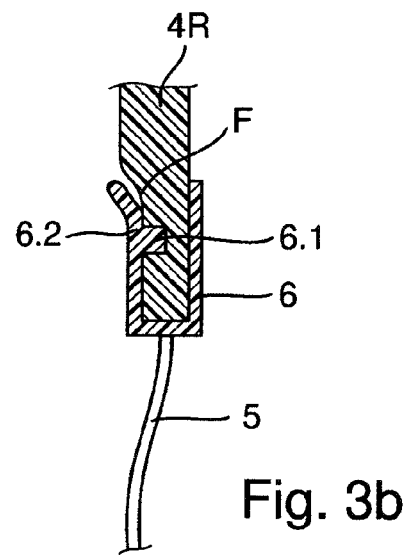
Figure 4A:
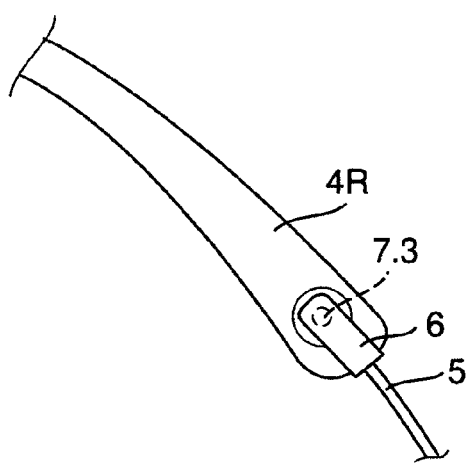
FIGS. 4a and 4b show a free end of the arm from the inside and from the outside.
Figure 4B:
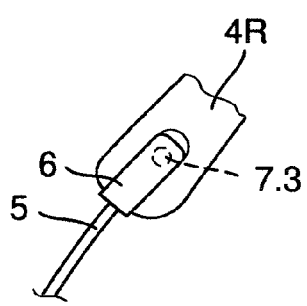

FIG. 3a shows a detail view of arm 4R and a cross section 3b. In the illustrated embodiment in FIG. 3a and FIG. 3b, receiving devices 7.1 are formed by holes, in which a plug 6.1 of connecting element 6 can engage. Groove F is easily recognizable in the cross section of FIG. 3b. Here, the attachment is accomplished by a catch 6.2, which engages and is released by a plug 6.1 in the rim or the arm by, e.g., raising edge 6.2 with a fingernail. So that retainer 6 has connecting element 6 and receiving device 7, which because of the requirement for many discrete holding points can be made linear, is also visible as little as possible without the retaining strap, it is attached expediently on the inner side of the arm. Possible negative effects on the user due to the attachment can be avoided by a depression (groove F), which assures a flush fit in the employed state. A receiving device 7.3, as shown in FIG. 4, is also attached at the end of the eyeglasses; this also has the advantage that a negative effect of a connecting element adjacent to the head on the inside can be ruled out. Overall, to avoid negative effects it is generally practical to make connecting element 6 delicate, which is possible with metal but also with various plastics. The depression for receiving device 7.3 can be made so that connecting element 6 is fixed in its position; therefore a predetermined angle or movement radius results between the free end of the arm and the connecting element. FIG. 4a shows a partial view of arm 4R from the inside, whereas FIG. 4b shows the same arm from the outside. The view from inside in FIG. 4a shows a crescent-shaped depression around the edge of the connecting element, in order to engage behind the edge and lever at the plug, e.g., with a fingernail and to release the snap connection.

Figure 5:
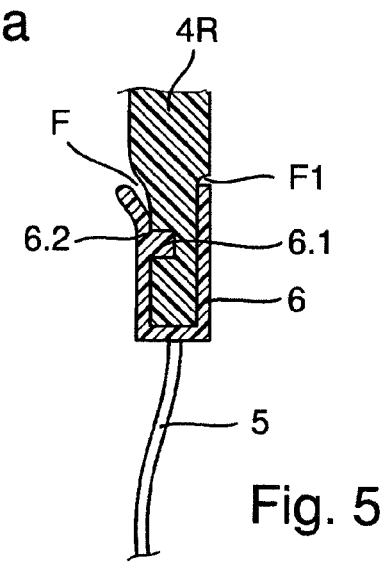
FIG. 5 shows a free end of the arm in cross section.

FIG. 5 shows a free end of arm 4R in cross section. Connecting element 6, as already described, has plug 6.1 and an edge 6.2. The free end of arm 4R has a depression on both sides to receive the two legs of connecting element 6. This produces a smooth finish of arm 4R. The connecting element is fixed in an angular position by the elongated depression in the arm.

In general, i.e., not only with regard to the free end of the arm, this solution is formed of a plug-/snap-in connection, as can also be provided at other positions along the arm. Here, as receiving device 7 a depression or a groove F (the female part) is provided on the inner side of the eyeglasses and optionally a groove 1 on the outer side of the eyeglasses, whereas a U-shaped retainer made of relatively rigid material, e.g., that of the eyeglasses or of metal, as part of connecting element 6 surrounds the arm and engages in the material, without penetrating it as in the plug connection described below. The connection can be detached again in the reverse order. The connection can be made round or as a groove and thereby rotatable between the eyeglasses and the connecting element or elongated as in FIG. 4 and thereby more rigid. The U-shaped part forms a connecting element of the retaining strap, which closes up a free end of the retaining strap. For the precise embodiment, reference is made as an example to DE 9320854 U1 cited above.

Other possible solutions for the detachable connection between arm 4R, 4L and connecting element 6 are shown below. Details can be obtained from WO 2011/076381 A1 of the same applicant, which is herein incorporated by reference. For example, detachable connections by means of a snap fastener, slotted hole, plug, or plug-/snap-in (plug) connection are shown there.

Figure 6A:
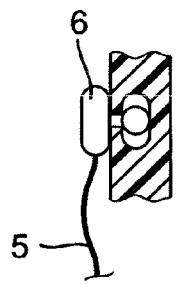
FIGS. 6a and 6b show a detachable connection by means of a snap fastener in two embodiments.
Figure 6B:
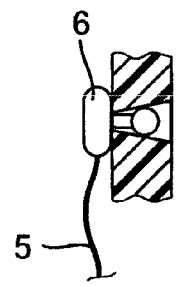

A first solution is a snap fastener connection (FIGS. 6a and 6b). Here, the opening (the female part) for the snap fastener as the receiving device is made on the inner side of the eyeglasses. In the realization in FIG. 6a the opening extends only approximately through half of the arm, whereas in the realization according to FIG. 6b it extends completely through the material. The first realization in FIG. 6a has the advantage that the outer side, therefore the visible side, of the arm conceals the snap fastener connection. Connecting element 6 is made as a stud with the snap fastener (the male part) of rigid material, e.g., like the eyeglasses. The connection between connecting element 6 and retaining strap 5 can occur by integral molding. Thus it can be achieved that the connection between the eyeglasses and retaining strap appears harmonious and as one piece.

Another solution is a slotted hole connection (without a figure). Here, at the free end of the arm or in another area of the eyeglasses a slotted hole opening is provided as the receiving device, said hole through which a plug of the connecting element passes and can be locked by moving in the slotted hole. The plug may have a flattened head, which fits into a depression on the arm. The plug is part of the connecting element and made of a hard material, such as, e.g., the eyeglasses, and connected to the retaining strap.

A further solution includes a plug connection (without a figure). Here, a connecting element part formed as a plug is inserted through a hole in the arm and attached with a U-shaped connecting loop of the connecting element, e.g., by a snap fastener-like connection. The U-shaped connecting strap with plug is part of the connecting element, is made of a hard material like, e.g., the eyeglasses, and is connected to the retaining strap.

Figure 7A:
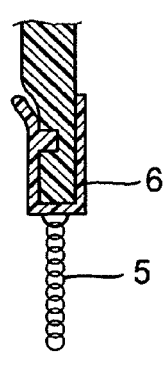
FIGS. 7a-7d show various connections between the connecting element and the retaining strap.
Figure 7B:
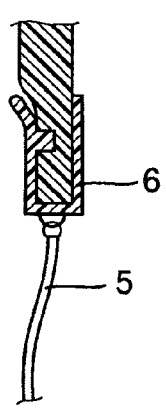
Figure 7C:
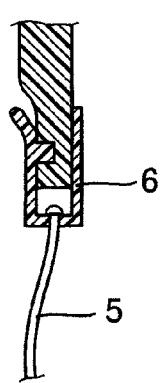
Figure 7D:
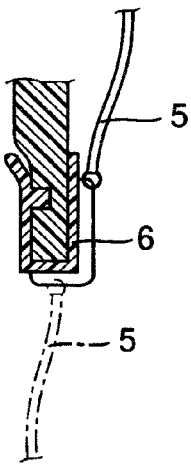

The attachment of connecting element 6 to retaining strap 5 occurs either, as in jewelry or necklaces, as between a clasp and chain, e.g., through an eyelet. This type of attachment is shown in FIGS. 7a-7c. Retaining strap 5 is formed as a chain in FIG. 7a. In FIG. 7b, retaining strap 5 at its free end has a ring with which it is attached to connecting element 6. In FIG. 7c retaining strap 5 penetrates connecting element 6 and is welded or glued to it.

In FIG. 7b, the connection, in which the retaining strap is guided movably on the connecting element by means of a wire, permits a substantially greater freedom of movement, so that the eyeglasses, e.g., when folded, may be worn hanging at the retaining strap with the top side facing upward.

Figure 8A:
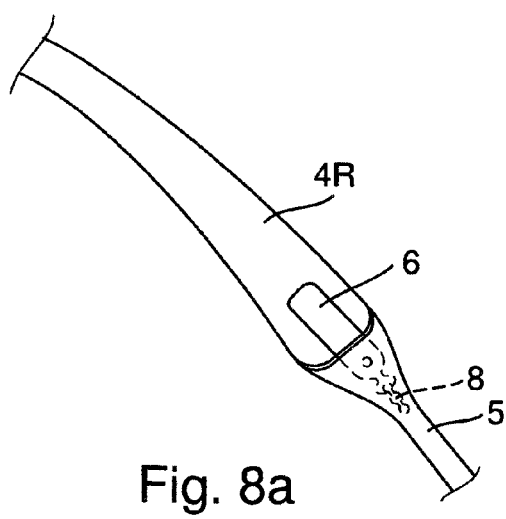
FIGS. 8a and 8b show an integral molding of the retaining strap to the connecting element.
Figure 8B:
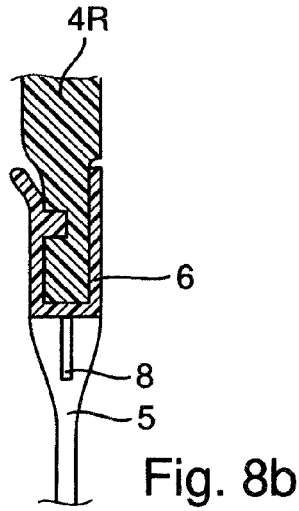

A form-fitting connection of an, e.g., elastic plastic of retaining strap 5 to a connecting element 6 is achieved in that retaining strap 5 is integrally molded to connecting element 6 with continuous material transitions and by internal serrations 8 or interpenetration. The outer view is shown in FIG. 8a and the cross section in FIG. 8b in the example of a retaining strap at a free end of an arm. It can also be achieved in this way that connecting element 6 is made of the same material as arm 4R.

In general, retaining strap 5 can be integrally molded to the hard material of connecting element 6, whereby connecting element 6 may be made from the same material as arm 4R, 4L.

The integral molding of retaining strap 5 is carried out so that the rigid end of connecting element 6 connects well with the sheathing, e.g., elastic material of retaining strap 5. This is assured in that the free end of connecting element 6 has serrations and additional openings through which the elastic material can connect. The serrations can also be formed, however, by a separate endpiece, e.g., made of metal, which is anchored in the connecting element. As a result, the retaining strap becomes an integral part of the eyeglasses, which creates many possibilities for the aesthetic design of glasses and retaining strap. Details of the connection between the retaining strap and connecting element can be obtained from WO 2011/076381 A1 of the same applicant, which is hereby incorporated by reference. During the "integral molding," the connection between two parts can be promoted by chemical dissolving or by thermal bonding, therefore by melting.

Many retaining straps from the state of the art are woven straps made of textile, nonelastic, and non-melting material. The preferred material is plastic, which should not rule out that plastic fibers can be woven to form a textile. According to the invention, plastic should also be used inter alia because the retaining strap should be elastic in a realization, so that the eyeglasses can be slipped over the head with a short retaining strap. Elastomers or still better thermoplastic elastomers such as, e.g., NBR, may be used as plastics. These are elastic, processable at moderate temperatures, retain their shape, and are resistant to aging. Suitable plastics are known from the literature.

Some figures show the retaining strap attached directly to the connecting element, e.g., FIGS. 3*a*, 3*b*, 4*a*, 4*b*, and 5. Of course, the retaining strap can also be attached to the connecting element by means of an eyelet and ring, as shown in FIG. 7*b*. Of course, the retaining strap can be formed not as a strap but as a chain, as is shown by way of example in FIG. 7*a*.

The eyeglasses of the invention with a retaining strap have several advantages: The connection between the retaining strap and eyeglasses is detachable, so that the eyeglasses can be worn with or without the retaining strap. The connection enables a plurality of different attachment points to the eyeglasses, to fulfill different requirements and preferences of the user. For this purpose, the arm has inconspicuous receiving seats for the retainer of the retaining strap, by means of which the retaining strap can be attached detachably but securely at many places. Although numerous designs to achieve this purpose are conceivable, those are given preference in which the receiving devices do not penetrate through the arm.

The receiving device on the eyeglasses is also not prominently visible when worn without the retaining strap, so that in principle these are eyeglasses that have the additional benefit that different retaining straps can be attached at different places.

One of the advantages of the invention is the positive aesthetic aspect of the eyeglasses. In particular, the retaining strap or the connecting element can be matched in material and color to the eyeglasses. The connection is made so that thereby very different retaining straps are conceivable, particularly elastic or non-elastic, inconspicuous straps or formed as a necklace. The connection between the eyeglasses and retaining strap is designed such that aesthetically a homogeneous unit between the two results.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. Eyeglasses comprising:
   a rim;
   an arm that is connected at a front end thereof to the rim,
   wherein a plurality of receiving devices being adapted to interact with a connecting element of a retaining strap are disposed between the front end and a free end of the arm at predetermined positions,
   wherein the connecting element forms a detachable connection with the arm, and
   wherein the plurality of receiving devices are not visible along an outer side of the arm on the outer side.

2. The eyeglasses according to claim 1, wherein the detachable connection is formed via a snap fastener, slotted hole, plug, or plug-/snap-in connection.

3. The eyeglasses according to claim 1, wherein the eyeglasses comprises two arms.

4. The eyeglasses according to claim 2, wherein the two arms mirror one another.

5. The eyeglasses according to claim 2, wherein the two arms are symmetrical to one another.

6. The eyeglasses according to claim 1, wherein the retaining strap is guided movably on the connecting element via rings traveling over a wire.

7. A retaining strap for interacting with eyeglasses according to claim 1, wherein a connecting element is attached undetachably, particularly is integrally molded, at at least one end of the retaining strap, wherein the connecting element interacts with a receiving device on the arm.

8. The retaining strap according to claim 6, wherein the connecting element is surrounded undetachably or penetrated by the material of the integrally molded retaining strap.

9. The retaining strap according to claim 7, wherein the connecting element has serrations or openings, which are surrounded or penetrated by the material of the integrally molded retaining strap.

10. The retaining strap according to claim 8, wherein the integral molding of the retaining strap to the connecting element occurs in the manner that a continuous transition to the connecting element results.

11. The retaining strap according to claim 9, wherein the connecting element is made of the same material as the arm.

12. Eyeglasses comprising:
    a rim;
    an arm that is connected at a front end thereof to the rim,
    wherein a plurality of receiving devices being adapted to interact with a connecting element of a retaining strap are disposed between the front end and a free end of the arm at predetermined positions,
    wherein the connecting element forms a detachable connection with the arm,
    wherein an outer side of the arm has no hole or only one hole at the free end of the arm, and
    wherein the plurality of receiving devices are not visible along the outer side of the arm on the outer side.

13. The eyeglasses according to claim 12, wherein the detachable connection is formed via a snap fastener, slotted hole, plug, or plug-/snap-in connection.

14. The eyeglasses according to claim 12, wherein the plurality of receiving devices are arranged in a groove or a hole formed on an inner side of the arm, and wherein the groove or hole does not extend to the outer side of the arm.

* * * * *